United States Patent [19]
Richard et al.

[11] Patent Number: 5,854,225
[45] Date of Patent: Dec. 29, 1998

[54] COMPOUNDS DERIVED FROM CYCLODEXTRIN

[75] Inventors: Herve Richard, Villepinte; Madeleine Leduc, Paris, both of France

[73] Assignee: L'Oreal, Paris, France

[21] Appl. No.: 747,334

[22] Filed: Nov. 12, 1996

[30] Foreign Application Priority Data

Nov. 13, 1995 [FR] France .................................. 95 13413

[51] Int. Cl.⁶ ........................ C08B 37/16; A61K 31/715
[52] U.S. Cl. .............................. 514/58; 536/103
[58] Field of Search ............................ 514/58, 951, 962, 514/970; 536/103; 424/461, 479, 937, 938

[56] References Cited

U.S. PATENT DOCUMENTS

| | | | |
|---|---|---|---|
| 3,565,887 | 2/1971 | Parmerter et al. | 536/103 |
| 4,727,064 | 2/1988 | Pitha | 514/58 |
| 5,180,716 | 1/1993 | Yaksh et al. | 514/58 |
| 5,198,429 | 3/1993 | König et al. | 514/58 |
| 5,464,827 | 11/1995 | Soll | 514/58 |
| 5,486,508 | 1/1996 | Uda et al. | 514/58 |
| 5,594,125 | 1/1997 | Seyschab et al. | 536/103 |
| 5,633,368 | 5/1997 | Hirsenkorn | 536/103 |
| 5,646,131 | 7/1997 | Badwan et al. | 514/58 |
| 5,654,422 | 8/1997 | Hirsenkorn | 536/103 |

*Primary Examiner*—Howard C. Lee
*Attorney, Agent, or Firm*—Finnegan, Henderson, Farabow, Garrett & Dunner, L.L.P.

[57] ABSTRACT

The invention relates to cyclodextrin derivatives of formula (I)

$$CD(OH)_l(OCOR)_m(OR_2)_n \quad (1)$$

in which each $R_1$ independently denotes a $C_6$–$C_{24}$ alkyl radical or a $C_8$–$C_{24}$ alkenyl radical, each $R_2$ independently denotes a $C_1$–$C_4$ alkyl or $C_2$–$C_4$ hydroxyalkyl radical, and I, m and n are statistical values. The invention also relates to a process for the preparation of the compounds of formula (I) and to the use of these compounds in cosmetics.

19 Claims, No Drawings

COMPOUNDS DERIVED FROM CYCLODEXTRIN

The present invention relates to new compounds derived from cyclodextrin, to the process for their preparation and to their use in cosmetics.

Cyclodextrins are oligosaccharides of formula

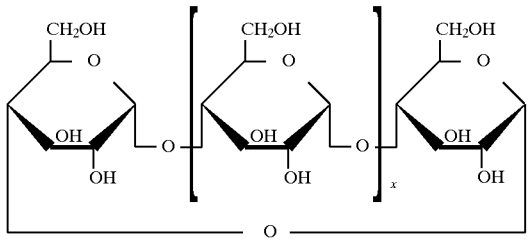

in which x may be a number equal to 4 (which corresponds to α-cyclodextrin), to 5 (β-cyclodextrin) or to 6 (γ-cyclodextrin).

Cyclodextrins are compounds which are well known, especially for their ability to form inclusion complexes with active substances. However, these compounds are not soluble in oils, and this limits their use in cosmetic compositions containing a fatty phase.

It is known to substitute the hydroxyl radicals of cyclodextrins with a view to modifying the properties of these compounds. Thus, U.S. Pat. No. 3,565,887 describes esters of cyclodextrins and of fatty acids which may be employed as a surface agent. However, the solubility of these compounds, in particular the solubility in oils, remains insufficient, and this limits their use, especially in cosmetic compositions. Availability of cyclodextrin derivatives which have a good solubility in oils continues to be a problem.

After various research on cyclodextrins, the inventors have surprisingly found that a new class of cyclodextrins makes it possible to overcome the disadvantages encountered hitherto.

The inventors found that the solubility of cyclodextrin derivatives in oils could be improved by grafting particular radicals onto the basic skeleton of cyclodextrins.

The subject-matter of the present invention is therefore new compounds derived from cyclodextrin, corresponding to the following general formula (I):

$$CD(OH)_l(OCOR_1)_m(OR_2)_n \qquad (1)$$

in which:

CD denotes a cyclodextrin base skeleton without the hydroxyl groups, wherein said cyclodextrin is α-, β-, or γ-cyclodextrin, $OCOR_1$ denotes a radical bonded to said cyclodextrin base skeleton, in which each $R_1$ independently denotes a radical selected from $C_6$–$C_{24}$ linear or branched alkyl radicals and $C_8$–$C_{24}$ linear or branched alkenyl radicals, $OR_2$ denotes a radical bonded to said cyclodextrin base skeleton, in which each $R_2$ independently denotes a radical comprising at least one radical selected from $C_1$–$C_4$ linear or branched alkyl radicals and $C_2$–$C_4$ hydroxyalkyl radicals, wherein the hydrogen of the hydroxyl radical of said hydroxyalkyl radical is optionally replaced with a radical comprising at least one radical selected from $C_2$–$C_4$ hydroxyalkyl radicals and -$COR_1$ radicals, m denotes the number of $OCOR_1$ radicals directly bonded to said cyclodextrin base skeleton and is a statistical value other than 0, n denotes the number of $OR_2$ radicals directly bonded to said cyclodextrin base skeleton and is a statistical value other than 0, and l denotes the number of hydroxyl groups bonded directly to said cyclodextrin base skeleton and is a statistical value, including zero, such that (l+m+n) is equal to 18, 21 or 24, according to whether said cyclodextrin of said base skeleton is α-, β- or γ-cyclodextrin, respectively, and further wherein the degree of substitution of cyclodextrin by radicals $R_1$ ranges from 0.2 to 1.

The new cyclodextrin derivatives offer the advantage of having better solubility in oils than that of the previously known derivatives. Besides the good solubility in oils, the compounds according to the invention have good surface-active properties enabling them to be employed in cosmetic compositions, especially as an emulsifying agent for the formulation of emulsions.

Within the scope of the present invention the degree of substitution of cyclodextrin by radicals $R_1$ is intended to mean the ratio of:

the number p of radicals $R_1$ originating, on the one hand, from the m radicals ($OCOR_1$) directly bonded to the base skeleton of cyclodextrin and, on the other hand, from the optional radicals -$COR_1$ bonded to the hydroxyalkyl radicals $R_2$ of the radical ($OR_2$), to the number (l+m+n) as defined above, which corresponds to the number of hydroxyl radicals present in a cyclodextrin which would be unsubstituted.

Thus, according to whether CD denotes the base skeleton of α-, β- or of γ-cyclodextrin, the degree of substitution is p/18, p/21 or p/24 respectively.

According to the invention the degree of substitution of cyclodextrin preferably ranges from higher than 0.4 to 1, and more preferably ranges from 0.45 to 0.95.

The value of p can be determined, for example, from the saponification value or from the NMR spectrum.

$R_1$ preferably denotes a $C_{11}$–$C_{21}$ linear or branched alkyl or alkenyl radical and preferably the radical $R_1$ taken in the radical -$COR_1$ may be chosen from lauryl, myristyl, palmityl, stearyl, behenyl, oleyl and linolenyl radicals and their mixtures.

$R_2$ preferably denotes a methyl or hydroxypropyl radical, it being possible for the hydrogen of the hydroxypropyl radical to be substituted by another hydroxypropyl radical or by a radical -$COR_1$ which may be chosen from lauryl, myristyl, palmityl, stearyl, behenyl, oleyl and linolenyl radicals and their mixtures. More preferably $R_2$ denotes a hydroxypropyl radical.

When CD denotes the base skeleton of α-cyclodextrin, the sum (l+m+n) is equal to 18, n preferably has a value ranging from 3 to 5, and the total number p of radicals $R_1$ preferably ranges from 3.6 to 18.

When CD denotes the base skeleton of β-cyclodextrin, the sum (l+m+n) being equal to 21, n is preferably a value ranging from 3 to 8, more preferably from 4 to 7, and most preferably a value equal to 4.2 or 6.3; the total number p of radicals $R_1$ preferably ranges from 4.2 to 21 and more preferably ranges from 10 to 21.

When CD denotes the base skeleton of γ-cyclodextrin, the sum (l+m+n) being equal to 24, n is preferably a value ranging from 4 to 8, the total number p of radicals $R_1$ ranging preferably from 4.8 to 24.

CD is preferably the base skeleton of β-cyclodextrin.

Another subject-matter of the present invention is a process for the preparation of the compounds of formula (I).

This process comprises reacting a cyclodextrin derivative of formula $CD(OR_2)_n(OH)_{l'}$, in which CD, $R_2$ and n have the same meaning as above, l' is a nonzero statistical value such that (l'+n) is equal to 18, 21 or 24, according to whether CD denotes the base skeleton of α-, β- or γ-cyclodextrin, with p moles of an acid chloride of formula Cl-CO-$R_1$, p and $R_1$ having the same meaning as above.

The reaction preferably may be performed in an organic, especially anhydrous, solvent such as pyridine or dimethylformamide.

The reaction preferably may be performed at a temperature ranging from 0° C. to 40° C. and more preferably from 10° C. to 25° C.

The reaction preferably may be performed in the presence of an acylation catalyst. The latter preferably may be para-N,N-dimethylaminopyridine.

Another subject-matter of the present invention is a composition including a compound of formula (I) as defined above or a mixture of these compounds.

The composition including the compound preferably may be in the form of a cosmetic, pharmaceutical or hygienic composition including a cosmetically, pharmaceutically or hygienically acceptable medium respectively.

In the compositions according to the invention the compounds of formula (I) preferably may be present in a concentration ranging from 0.1% to 10% by weight and more preferably from 0.5% to 5% by weight relative to the total weight of the composition.

The compounds according to the invention preferably may be present in the composition in the form of an aqueous or organic solution or dispersion, or even in the form of vesicular dispersion or of a dispersion of nanospheres or nanocapsules.

These compositions may additionally include the ingredients usually employed in the field in question. They may thus contain at least one constituent chosen from fatty substances, thickeners, fatty acid esters, esters of fatty acids and of glycerol, silicones (volatile or otherwise, functionalized or otherwise), fatty alcohols, surfactants, perfumes, preservatives, sunscreens, proteins, vitamins, polymers, organic or inorganic oils, pigments, fillers and any other additive traditionally employed in the cosmetic, pharmaceutical or hygiene field.

These compositions may be prepared according to the usual methods known to the person skilled in the art. They preferably may be in the form of gel, of water-in-oil or oil-in-water emulsion, of solid stick, of spray or of aerosol foam.

Another subject-matter of the invention is the use of the compounds of formula (I) as defined above as a surface-active agent, especially in the context of the formation of emulsion, preferably of an oil-in-water or water-in-oil emulsion, and more particularly as an emulsifying agent.

The compounds according to the invention may also be employed as an agent for encapsulation, especially of cosmetic, pharmaceutical or hygienic active substances.

They may be employed in compositions for cleaning the skin or hair for trapping and encapsulating especially the constituents of sebum of the skin or of the scalp. In particular, they may be employed as a skin-matting agent.

One subject of the invention is therefore the use of the compounds of formula (I) as an encapsulating agent.

Another subject of the invention is the use of the compounds of formula (I) as an agent for cleaning the skin and/or hair in a cosmetic or hygienic composition.

A number of examples for the preparation of compounds according to the invention and examples of cosmetic compositions including them will now be given by way of illustration and without any limitation being implied.

EXAMPLES

EXAMPLE 1

Preparation of a compound of formula (I) in which $R_1$ is a stearyl radical, $R_2$ is a hydroxypropyl radical, n=6.3 and p=14

52.5 g (173 mmol) of stearyl chloride were added dropwise for 20 minutes at 20° C. to a solution of 12.4 g (8.3 mmol) of hydroxypropyl-β-cyclodextrin (n=6.3), sold by the company Aldrich, in 100 ml of anhydrous pyridine. After 5 hours' stirring at ambient temperature, the reaction mixture was poured into 400 ml of ethanol. The solid obtained was filtered off and washed three times with 200 ml portions of hot ethanol.

After drying, 40.5 g of a light-beige solid which had a melting point of 39° C. were obtained.

Infrared: ester band at 1745 cm$^{-1}$

EXAMPLE 2

Preparation of a compound of formula (I) in which $R_1$ is a stearyl radical, $R_2$ is a hydroxypropyl radical, n=4.2 and p=14

The compound was prepared according to the procedure of Example 1, by employing:

6.9 g (5 mmol) of hydroxypropyl-β-cyclodextrin (n=4.2), sold under the name RHODOCAP HP by the company Rhône-Poulenc, and 31.8 g (105 mmol) of stearyl chloride.

28.8 g of a light-beige solid which had a melting point of 41° C. were obtained.

Infrared: ester band at 1745 cm$^{-1}$

EXAMPLE 3

Preparation of a compound of formula (I) in which $R_1$ is an oleyl radical, $R_2$ is a hydroxypropyl radical, n=4.2 and p=17

The compound was prepared according to the procedure of Example 1, by employing:

6.9 g (5 mmol) of hydroxypropyl-β-cyclodextrin (n=4.2), and 31.6 g (105 mmol) of oleyl chloride.

The reaction mixture was poured into 150 ml of ethanol. The lower phase was extracted and washed twice with 150 ml portions of ethanol and was then taken up in dichloromethane. After drying and evaporation of the organic phase, 24 g of a brown oil were obtained.

Infrared: ester band at 1745 cm$^{-1}$

EXAMPLE 4

Preparation of a compound of formula (I) in which $R_1$ is a palmityl radical, $R_2$ is a hydroxypropyl radical, n=4.2 and p=10

The compound was prepared according to the procedure of Example 1, by employing:

6.9 g (5 mmol) of hydroxypropyl-β-cyclodextrin (n=4.2), and 13.8 g (50 mmol) of palmityl chloride.

11.5 g of a white transparent solid which had a softening point of 75° C. were obtained.

Infrared: ester band at 1745 cm$^{-1}$

EXAMPLE 5

Preparation of a derivative of formula (I) in which $R_1$ is a palmityl radical, $R_2$ is a hydroxypropyl radical, n=4.2 and p=19

The compound was prepared according to the procedure of Example 1, by employing:

6.9 g (5 mmol) of hydroxypropyl-β-cyclodextrin (n=4.2) to which are added 4.88 g (40 mmol) of 4-dimethylaminopyridine, and 28.9 g (105 mmol) of palmityl chloride.

Stirring was continued at ambient temperature for 17 hours. 28.9 g (105 mmol) of palmityl chloride were then added again dropwise over 20 minutes and stirring was continued at 60° C. for 6 hours.

After treatment of the reaction mixture 29.1 g of a light-beige solid which had a melting point of 41°–43° C. were obtained.

Infrared: ester band at 1745 cm$^{-1}$

EXAMPLE 6

Preparation of a derivative of formula (I) in which $R_1$ is a myristyl radical, $R_2$ is a hydroxypropyl radical, n=4.2 and p=19

The compound was prepared according to the procedure of Example 1, by employing:
- 18.22 g (13.2 mmol) of hydroxypropyl-β-cyclodextrin (n=4.2), and
- 68.4 g (277 mmol) of myristyl chloride.

40 g of a pale yellow gum were obtained.

Infrared: ester band at 1745 cm$^{-1}$

EXAMPLE 7

Preparation of a compound of formula (I) in which $R_1$ is a lauryl radical, $R_2$ is a hydroxypropyl radical, n=4.2 and p=18

The compound was prepared according to the procedure of Example 1, by employing:
- 18.22 g (13.2 mmol) of hydroxypropyl-β-cyclodextrin (n=4.2), and
- 60.6 g (277 mmol) of lauryl chloride.

29 g of a pale yellow gum were obtained.

Infrared: ester band at 1745 cm$^{-1}$

EXAMPLE 8 (COMPARATIVE)

Preparation of a derivative of formula (I) in which $R_1$ is a stearyl radical, n=0 and p=14 (a compound which does not come within the scope of the invention)

The compound was prepared according to the procedure of Example 1, by employing:
- 15 g (13.2 mmol) of β-cyclodextrin, and
- 83.9 g (277 mmol) of stearyl chloride.

The heterogeneous mixture was kept stirred at ambient temperature for 18 hours.

After treatment of the reaction mixture, 62.5 g of a broken-white solid which had a melting point of 50° C. were obtained.

Infrared: ester band at 1745 cm$^{-1}$

EXAMPLE 9 (COMPARATIVE)

Preparation of a derivative of formula (I) in which $R_1$ is a palmityl radical, n=0 and p=21 (a compound which does not come within the scope of the invention)

The compound was prepared according to the procedure of Example 7, by employing:
- 5.7 g (5 mmol) of β-cyclodextrin and 4.88 g (40 mmol) of 4-dimethylaminopyridine, and
- 2×28.9 g (2×105 mmol) of palmityl chloride.

After addition of the first fraction of acid chloride, stirring was continued at ambient temperature for 23 hours. After addition of the second fraction of acid chloride, stirring was continued at ambient temperature for 6 hours.

After treatment of the reaction mixture, 22.5 g of a beige-yellow wax which had a melting point of 51° C. were obtained.

Infrared: ester band at 1745 cm$^{-1}$

EXAMPLE 10 (COMPARATIVE)

Preparation of a derivative of formula (I) in which $R_1$ is a stearyl radical, $R_2$ is a hydroxypropyl radical, n=4.2 and p=3 (a compound which does not come within the scope of the invention)

The compound was prepared according to the procedure of Example 1, by employing:
- 1.38 g (1 mmol) of hydroxypropyl-β-cyclodextrin (n=4.2), and
- 1.4 g (4.6 mmol) of stearyl chloride.

After purification of the crude reaction product by chromatography on silica (eluent 95/5 dichloromethane/methanol), 1.8 g of a beige powder which had a softening point of 135° C. were obtained.

Infrared: ester band at 1745 cm$^{-1}$

EXAMPLE 11

Test for solubility in oils

The solubility of the compounds according to the invention of Examples I to 7 and that of the comparative compounds 8 to 10 was determined, on the one hand in liquid petrolatum, on the other hand in MIGLYOL 812 from the company Dynamit-Nobel (capric/caprylic acid triglycerides).

The solubility was determined by the maximum quantity of compound which could be dissolved in the test oil and is expressed as percentage weight/weight.

The following results were obtained:

| Example | $R_2$ | n | p | p/21 | Miglyol % | Liquid petrolatum % |
|---|---|---|---|---|---|---|
| 1 | HP | 6.3 | 14 | 0.66 | 12 | 12 |
| 2 | HP | 4.2 | 14 | 0.66 | 9 | 7 |
| 3 | HP | 4.2 | 17 | 0.81 | >50 | >50 |
| 4 | HP | 4.2 | 10 | 0.48 | 6 | 8 |
| 5 | HP | 4.2 | 19 | 0.90 | 8 | 12 |
| 6 | HP | 4.2 | 19 | 0.90 | >35 | >20 |
| 7 | HP | 4.2 | 18 | 0.86 | >20 | >30 |
| 8(c) | — | 0 | 14 | 0.66 | 1 | 1 |
| 9(c) | — | 0 | 21 | 1 | 1.5 | 2 |
| 10(c) | HP | 4.2 | 3 | 0.14 | <1 | <1 |

HP: hydroxypropyl
(c): comparative

It was found that only the compounds in accordance with the invention (Examples 1 to 7) have a solubility in oils which is higher than 5%.

In particular, the results of solubility of the compounds of Examples 1, 2 and 8 show that, in the case of the compounds which are substituted identically by radicals $R_1$ at C17, only those which are also substituted by hydroxypropyl radicals have a very good solubility in oils.

When the solubility of the compound of Example 10 was compared with that of the compounds of Examples I to 7, it was found that when the degree of substitution is equal to 0.14, the compound is poorly soluble in oils (Example 10), whereas when the degree of substitution is of the order of 0.48 or higher the compounds are well soluble in oils.

EXAMPLE 12

The ability of the compound of Example 1 to modify the water/liquid petrolatum interfacial tension was determined by the Leconte du Nouy ring method. This method consists of determining the reaction force exerted by a solution of the compound of Example 1 on a ring which passes through the interface.

The interfacial tension, at 25° C., was measured between, on the one hand, water and liquid petrolatum and between water and a solution containing 1% of the compound of Example 1 in liquid petrolatum. A measurement was performed at $t_0$ just after both phases had been placed in contact and at $t_1$ 1 hour after both phases had been placed in contact.

The following results were obtained:

|  | Interfacial tension at $t_0$ | Interfacial tension at $t_1$ |
| --- | --- | --- |
| Water/liquid petrolatum | 48.8 mN/m | 48 mN/m |
| Water/liquid petrolatum + 1% of the compound of Ex. 1 | 22.4 mN/m | 19.5 mN/m |

It was found that when the compound of Example 1 was added to liquid petrolatum it lowered the water/liquid petrolatum interfacial tension at $t_0$ and at $t_1$. This compound therefore exhibits a surface-active character.

EXAMPLE 13

An oil-in-water emulsion was prepared which had the following composition:

| Compound of Example 1 | 1.5 g |
| --- | --- |
| Nonionic surfactants | 5.95 g |
| Silicone oil | 7 g |
| Hydrogenated polyisobutylene | 6 g |
| Thickening agent | 0.9 g |
| Sequestering agent | q.s. |
| Preservatives | q.s. |
| Water | q.s. for 100 g |

EXAMPLE 14

An emulsion was prepared which had the following composition:

| Compound of Example 3 | 1 g |
| --- | --- |
| Oils | 20.5 g |
| Emulsifying agents | 6.5 g |
| Stearic acid | 0.4 g |
| Glycerine | 3 g |
| Ethyl alcohol | 10 g |
| Preservatives | q.s. |
| Water | q.s. for 100 g |

A cream was obtained which could be employed for facial care against wrinkles.

EXAMPLE 15

A water-in-oil emulsion was prepared which had the following composition:

| Compound of Example 2 | 1 g |
| --- | --- |
| Liquid petrolatum | 4 g |
| Vegetable oil | 6 g |
| Emulsifying agent | 15 g |
| Glycerine | 5 g |
| Magnesium sulphate | 1 g |
| Water | q.s. for 100 g |

EXAMPLE 16

An oil-in-water emulsion was prepared which had the following composition:

| Compound of Example 2 | 0.5 g |
| --- | --- |
| Emulsifying agent | 3 g |
| Stearic acid | 0.7 g |
| Oils | 15 g |
| Sucrose stearate | 1.3 g |
| Glycerine | 2 g |
| Hexylene glycol | 4 g |
| Water | q.s. for 100 g |

EXAMPLE 17

A dispersion of nanoparticles was prepared according to the following procedure.

0.2 g of the compound of Example 7 were dissolved in 175 ml of acetone and a solution of 0.015 g of β-carotene dissolved in 25 ml of acetone was then added. A phase A was thus obtained.

An aqueous solution was also prepared containing 0.25 g of polyoxyethylene/polyoxypropylene block polymer sold under the name PLURONIC F68 by the company BASF and 100 g of water. This solution constituted phase B.

Phases A and B were heated to 50° C. and then phase A was poured into phase B with stirring. The mixture was then evaporated under reduced pressure to a weight of 40 g.

A translucent dispersion of nanospheres was thus obtained, the mean size of the nanospheres being 330 nm.

We claim:

1. A compound corresponding to the following general formula (I):

$$CD(OH)_l(O\text{-}C(O)\text{-}R_1)_m(OR_2)_n \qquad (1)$$

in which
  CD denotes a cyclodextrin base skeleton without the hydroxyl groups, wherein said cyclodextrin is α-, β- or γ-cyclodextrin,
  O-C(O)-$R_1$ denotes a radical bonded to said cyclodextrin base skeleton, in which each $R_1$ independently denotes a radical selected from $C_{11}$–$C_{24}$ linear or branched alkyl radicals and $C_{11}$–$C_{24}$ linear or branched alkenyl radicals,
  $OR_2$ denotes a radical bonded to said cyclodextrin base skeleton, in which each $R_2$ independently denotes a radical selected from $C_{1\text{-}C4}$ linear or branched alkyl radicals and $C_{2\text{-}C4}$ hydroxyalkyl radicals, wherein the hydrogen of the hydroxyl radical of said hydroxyalkyl radical is optionally replaced with a radical comprising at least one radical selected from $C_{2\text{-}C4}$ hydroxyalkyl radicals and -$COR_1$ radicals,
  m denotes the number of O-C(O)$R_1$ radicals directly bonded to said cyclodextrin base skeleton and is a statistical value other than 0, n denotes the number of OR$_2$ radicals directly bonded to said cyclodextrin base skeleton and is a statistical value other than 0, and l denotes the number of hydroxyl groups bonded directly to said cyclodextrin base skeleton and is a statistical value, including 0, such that (l+m+n) is equal to 18, 21 or 24, according to whether said cyclodextrin of said base skeleton is α-, β- or γ-cyclodextrin, respectively, and further wherein the degree of substitution of cyclodextrin by radicals R$_1$ ranges from 0.2 to 1.

2. A compound according to claim 1, wherein each R$_1$ independently is a radical comprising at least one radical selected from C$_{11}$–C$_{21}$ linear or branched alkyl radicals and C$_{11}$–C$_{21}$ linear or branched alkenyl radicals.

3. A compound according to claim 1, wherein each R$_1$ independently is a radical comprising at least one radical selected from lauryl, myristyl, palmityl, stearyl, behenyl, oleyl and linolenyl radicals.

4. A compound according to claim 1, wherein each R$_2$ independently denotes a methyl or hydroxypropyl radical, wherein the hydrogen of the hydroxyl radical of said hydroxypropyl radical is substituted by another hydroxypropyl radical or by a radical COR$_1$, wherein each R$_1$ is as defined in claim 1.

5. A compound according to claim 1, wherein CD denotes a β-cyclodextrin base skeleton.

6. A compound according to claim 1, wherein the degree of substitution of cyclodextrin by the radicals R$_1$ ranges from higher than 0.4 to 1.

7. A compound according to claim 6, wherein the degree of substitution of cyclodextrin by the radicals R$_1$ ranges from 0.45 to 0.95.

8. A compound according to claim 1, wherein CD denotes a β-cyclodextrin base skeleton and n ranges from 3 to 8.

9. A compound according to claim 8, wherein n ranges from 4 to 7.

10. A compound according to claim 9, wherein the total number of radicals R$_1$ ranges from 4.2 to 21.

11. A compound according to claim 10, wherein the total number of radicals R$_1$ ranges from 10 to 21.

12. A method for the preparation of a compound of formula (I)

$$CD(OH)_l(O\text{-}C(O)\text{-}R_1)_m(OR_2)_n \qquad (1)$$

wherein

CD denotes a cyclodextrin base skeleton without the hydroxyl groups, wherein said cyclodextrin is α-, β- or γ-cyclodextrin, O-C(O)-R$_1$ denotes a radical bonded to said cyclodextrin base skeleton, in which each R$_1$ independently denotes a radical selected from C$_{11}$–C$_{24}$ linear or branched alkyl radicals and C$_{11}$–C24 linear or branched alkenyl radicals, OR$_2$ denotes a radical bonded to said cyclodextrin base skeleton, in which each R$_2$ independently denotes a radical selected from C$_1$–C$_4$ linear or branched alkyl radicals and C$_2$–C$_4$ hydroxyalkyl radicals, wherein the hydrogen of the hydroxyl radical of said hydroxyalkyl radical is optionally replaced with a radical comprising at least one radical selected from C$_2$–C$_4$ hydroxyalkyl radicals and -COR$_1$ radicals, m denotes the number of O-C(O)-R$_1$ radicals directly bonded to said cyclodextrin base skeleton and is a statistical value other than 0, n denotes the number of OR$_2$ radicals directly bonded to said cyclodextrin base skeleton and is a statistical value other than 0, and l denotes the number of hydroxyl groups bonded directly to said cyclodextrin base skeleton and is a statistical value, including 0, such that (l+m+n) is equal to 18, 21 or 24, according to whether said cyclodextrin of said base skeleton is α-, β- or γ-cyclodextrin, respectively, and further wherein the degree of substitution of cyclodextrin by radicals R$_1$ ranges from 0.2 to 1, comprising the step of reacting (a) a cyclodextrin derivative of formula CD(OR$_2$)$_n$(OH)$_{l'}$, in which CD, OR$_2$, and n are as defined above and l' denotes the number of hydroxyl radicals bonded directly to said cyclodextrin base skeleton and is a nonzero statistical value such that (l'+n) is equal to 18, 21 or 24, according to whether said cyclodextrin of said base skeleton is α-, β- or γ-cyclodextrin, respectively with (b) p moles of an acid chloride of formula Cl-CO-R$_1$, wherein R$_1$ is as defined above and p is the total number of radicals R$_1$ under conditions sufficient to form said compound of formula (I).

13. A composition comprising at least one compound of formula (I) as defined in claim 1.

14. A composition according to claim 13, further comprising at least one medium selected from cosmetically, pharmaceutically and hygienically acceptable media.

15. A composition according to claim 13, wherein said compound of formula (I) is present in a concentration ranging from 0.1% to 10% by weight relative to the total weight of the composition.

16. A composition according to claim 13, wherein said compound of formula (I) is in the form of solution, dispersion, vesicular dispersion, dispersion of nanospheres or dispersion of nanocapsules.

17. A method of preparing a composition comprising the step of including in said composition at least one compound of formula (I) according to claim 1 as a surface-active agent.

18. A method of preparing an encapsulated cosmetic, pharmaceutical or hygienic active substance, comprising the step of encapsulating said cosmetic, pharmaceutical or hygienic active substance with an encapsulating agent comprising at least one compound of formula (I) according to claim 1.

19. A method of preparing a cosmetic or hygienic composition comprising the step of including in said composition an agent for cleaning the skin, hair, or skin and hair, wherein said agent comprises at least one compound of formula (I) according to claim 1.

* * * * *

UNITED STATES PATENT AND TRADEMARK OFFICE
CERTIFICATE OF CORRECTION

PATENT NO. : 5,854,225
DATED : December 29, 1998
INVENTOR(S) : Hervé RICHARD et al.

It is certified that error appears in the above-identified patent and that said Letters Patent is hereby corrected as shown below:

TITLE PAGE:

ITEM [57], in the Abstract
   line 3, "$CD(OH)_l(OCOR)_m(OR_2)_n$" should read --$CD(OH)_1(OCOR_1)_m(OR_2)_n$-- and
       "(1)" should read --(I)--;
   line 6, "I," should read --1,--.

IN THE CLAIMS:

Claim 1, col. 8, line 45, in the formula, "$(OH)_l$" should read --$(OH)_1$--; and
       "(1)" should read --(I)--;
   line 59, "$C_{1-C4}$" should read --$C_1$-$C_4$--;
   line 60, "$C_{2-C4}$" should read --$C_2$-$C_4$--;
   line 63, "$C_{2-C4}$" should read --$C_2$-$C_4$--;
col 9, line 4, "I" should read --1--; and
       line 6, "(I+m+n)" should read --(1+m+n)--.

UNITED STATES PATENT AND TRADEMARK OFFICE
CERTIFICATE OF CORRECTION

PATENT NO. : 5,854,225
DATED : December 29, 1998
INVENTOR(S) : Herve RICHARD et al.

It is certified that error appears in the above-identified patent and that said Letters Patent is hereby corrected as shown below:

Claim 12, col. 9, line 44, in the formula, "$(OH)_l$" should read --$(OH)_1$--; and
"(1)" should read --(I)--;
line 53, "$C_{ll} - C24$" should read --$C_{11} - C_{24}$;
line 58, "$C_{2-C4}$" should read --$C_2 - C_4$--;
col. 10, line 2, "$C_{2-c}4$" should read --$C_2 - C_4$--;
line 11, "I" should read --1--;
line 13, "(I+m+n)" should read --(1+m+n)--;
line 17, "0.2to" should read --0.2 to--;
line 19, in the formula, "$(OH)_l$" should read --$(OH)_1$--;

line 23, "(I'+n)" should read --(1'+n)--; and
line 26, "$CI-CO-R_1$" should read --$Cl-CO-R_1$--.

Signed and Sealed this

Eighth Day of June, 1999

Q. TODD DICKINSON

*Attest:*

*Attesting Officer*         Acting Commissioner of Patents and Trademarks